United States Patent [19]

David et al.

[11] 4,106,909
[45] Aug. 15, 1978

[54] CHEMICAL ANALYSIS WITH COATED, LIGHT WAVEGUIDE UNDER HUMIDITY CONTROL

[75] Inventors: Donald J. David, Centerville; Michael C. Willson, Waynesville, both of Ohio

[73] Assignee: Monsanto Research Corporation, St. Louis, Mo.

[21] Appl. No.: 781,596

[22] Filed: Mar. 28, 1977

Related U.S. Application Data

[60] Division of Ser. No. 724,482, Sep. 20, 1976, Pat. No. 4,040,691, which is a continuation-in-part of Ser. No. 689,403, May 24, 1976, abandoned.

[51] Int. Cl.² ............... G01N 21/00; G01N 21/46
[52] U.S. Cl. ............... 23/232 R; 23/230 R; 23/254 R
[58] Field of Search ............... 23/230 R, 232 R

[56] References Cited

U.S. PATENT DOCUMENTS

| | | | |
|---|---|---|---|
| 3,704,060 | 11/1972 | McNaney | 350/336 |
| 3,904,371 | 9/1975 | Neti | 23/232 R |
| 3,960,495 | 6/1976 | Tantram | 23/232 R |
| 4,003,707 | 1/1977 | Lubbers | 23/232 R |

Primary Examiner—Sidney Marantz
Attorney, Agent, or Firm—Bruce Stevens

[57] ABSTRACT

A coated waveguide holder-humidifier to supply moisture in the case of moisture-sensitive reactions in order that quantitative results might be obtained with a gradient light analytical detector which will quantitatively measure atmospheric contaminants by comparing changes in light transmission through the coated waveguides before and after exposure. The coated waveguide holder-humidifier comprises a container, a porous material capable of absorbing water and desorbing water vapor mounted within the container, means to hold one or more waveguides within the container, and one or more openings in the container to allow fluid (liquid or gas) sample to contact a waveguide. Also, a method for improving the sensitivity of gaseous reactants on a waveguide where the reaction is moisture sensitive comprising humidifying the environment of said waveguide providing an atmosphere which has a substantially constant humidity normally in the range of 85 to 100% at which said reaction is not appreciably affected by changes in ambient relative humidity.

2 Claims, 6 Drawing Figures

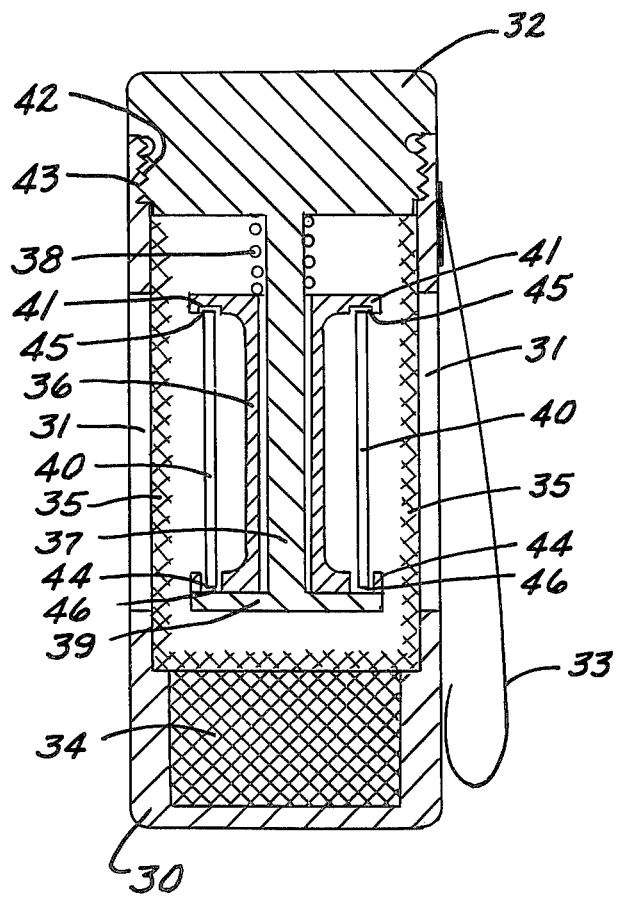
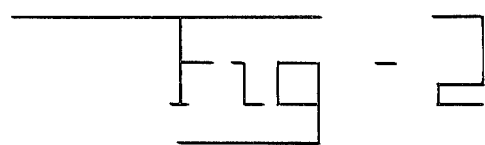

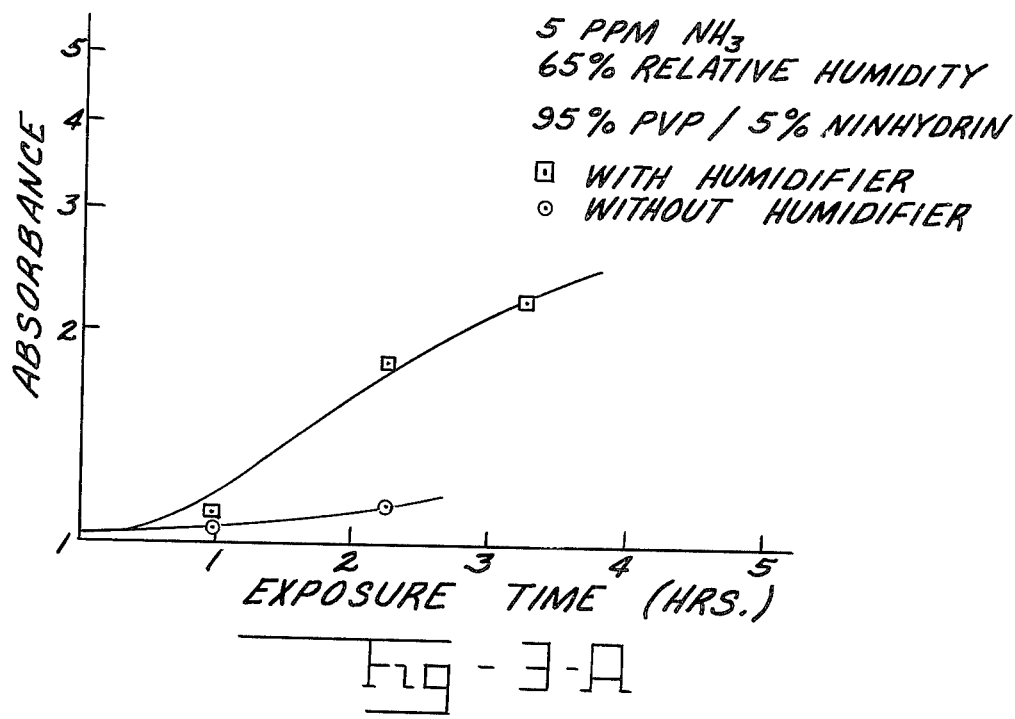
Fig-3-A
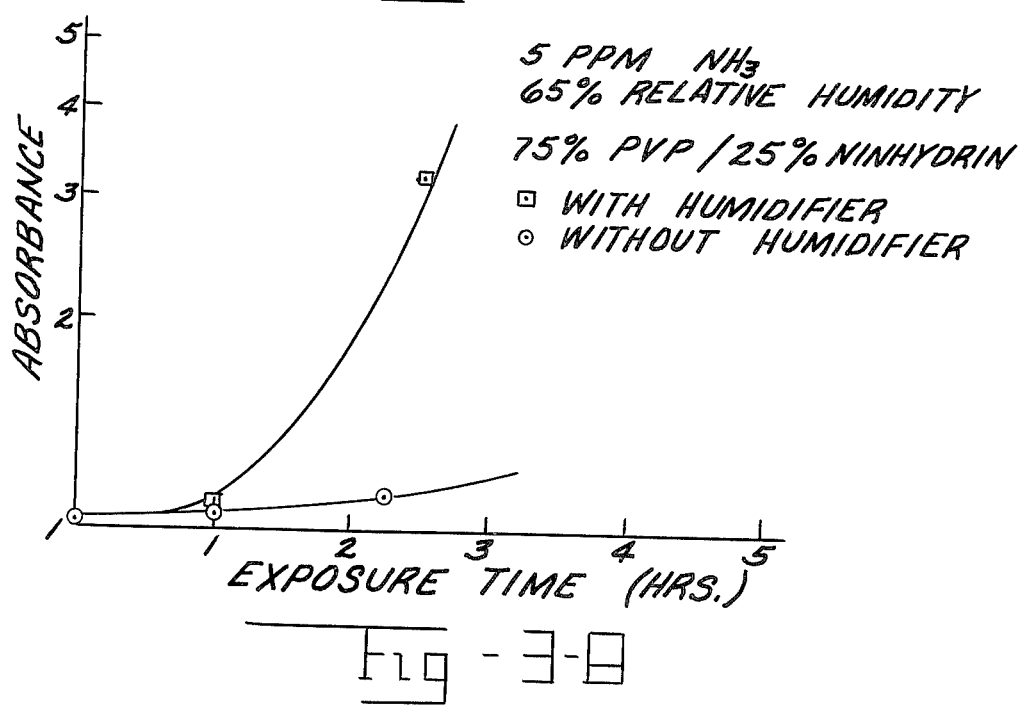
Fig-3-B

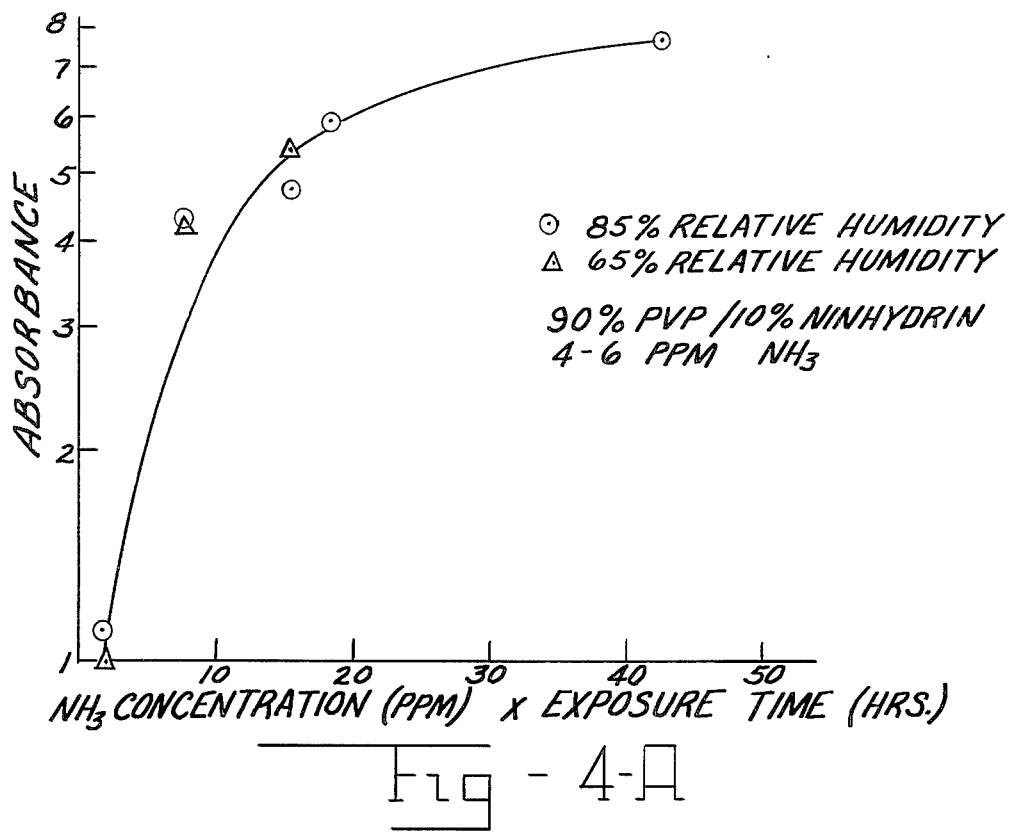
Fig - 4-A
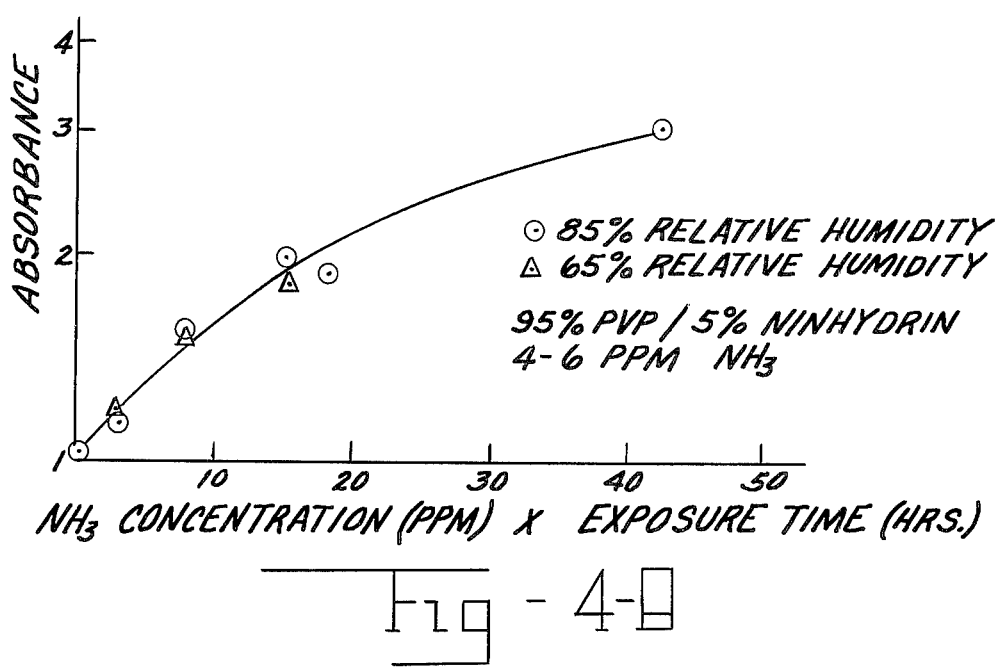
Fig - 4-B 4,106,909

CHEMICAL ANALYSIS WITH COATED, LIGHT WAVEGUIDE UNDER HUMIDITY CONTROL

CROSS-REFERENCE TO RELATED APPLICATIONS

This is a division of application Ser. No. 724,482, filed Sept. 20, 1976, now U.S. Pat. No. 4,040,691; which is a continuation-in-part of application Ser. No. 689,403, filed May 24, 1976, now abandoned.

This invention can be used with the Optical Analytical Device described in copending application Ser. No. 617,120, filed Sept. 26, 1975, now abandoned.

BACKGROUND OF THE INVENTION

The Field of the Invention is analytical chemistry apparatus.

SUMMARY OF THE INVENTION

This invention is a coated waveguide holder-humidifier which is used to supply moisture in the case of moisture sensitive reactions in order that quantitative results might be obtained with a gradient light analytical detector which will quantitatively measure atmospheric contaminants by comparing changes in light transmission through the coated waveguides before and after exposure. The coated waveguide holder-humidifier comprises a container, a porous material capable of absorbing water and desorbing water vapor mounted within the container, means to hold one or more waveguides within the container, and one or more openings in the container to allow fluid (liquid or gas) sample to contact a waveguide. Also the invention is a method for improving sensitivity of gaseous reactants on a waveguide where the reaction is moisture sensitive comprising humidifying the environment of said waveguide providing an atmosphere which has a substantially constant humidity normally in the range of 85% to 100% at which said reaction is not appreciably affected by changes in ambient relative humidity.

FIG. 2 is a sectional view of another embodiment of the invention,

FIG. 3A and FIG. 3B are graphical presentations of data obtained using an optical analytical device to measure ammonia with and without the use of the humidifier, and FIG. 4A and FIG. 4B are graphical presentations of data obtained using an optical analytical device to measure ammonia at different relative humidities and ninhydrin loadings on the waveguides with the use of the humidifier.

DESCRIPTION OF THE PREFERRED EMBODIMENTS

Figure 1:
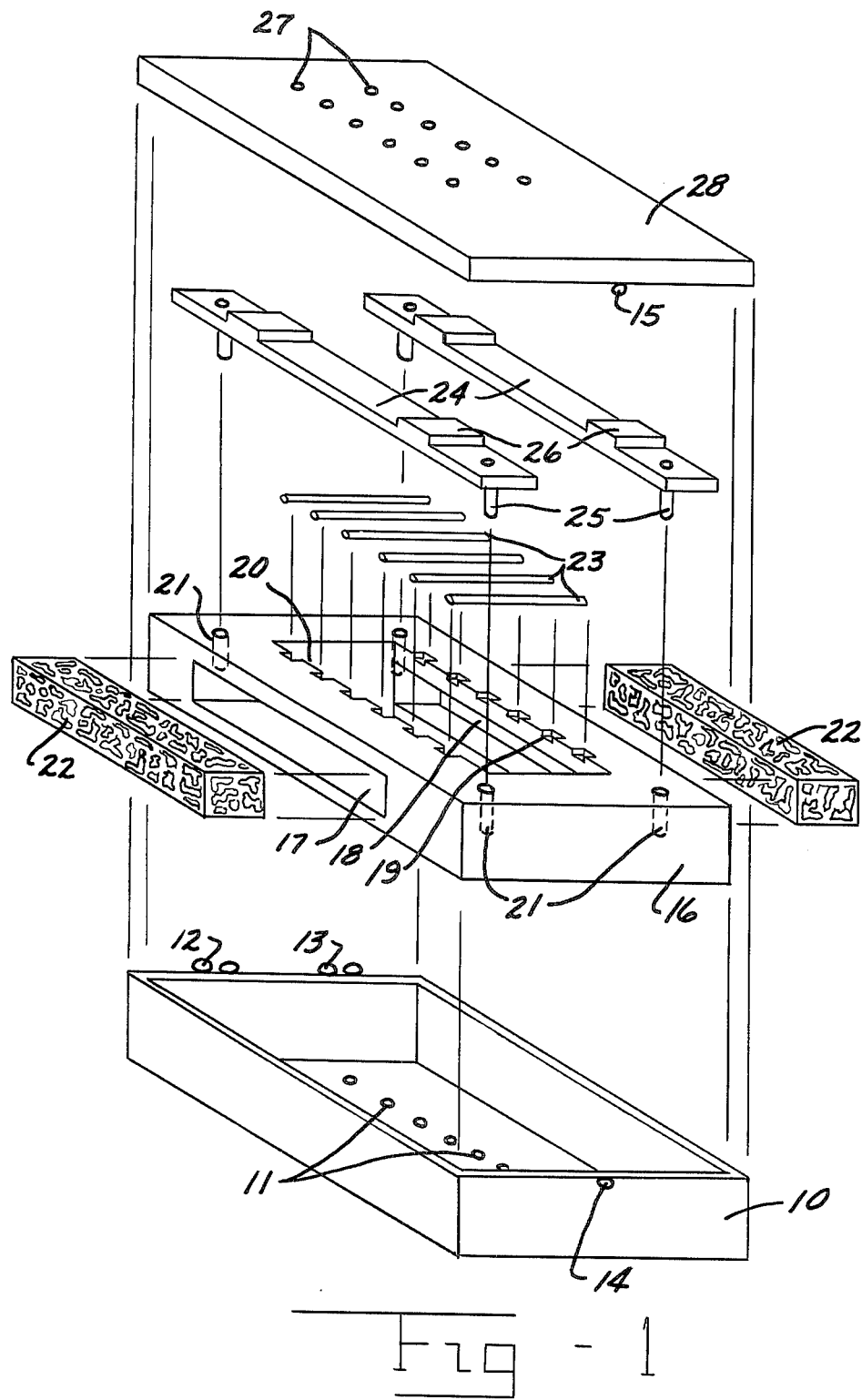
FIG. 1 is an exploded view of one embodiment of the invention.

A particular object of this invention is to provide a waveguide holder capable of supplying moisture to the waveguides which effectively increases the sensitivity of a gradient light analytical detector for those reactions sensitive to moisture such as the determination of ammonia in air and so provides loss dependence on relative humidity changes.

Another object of this invention is to provide a method for improving sensitivity of gaseous reactants on a waveguide where the reaction is moisture sensitive.

This and other objects of the invention will become apparent as the detailed description of the invention proceeds.

The moisture is applied to the container which holds the waveguides and at the same time free flow of the sample stream to the container is provided. The waveguides can be of any convenient shape and size but for greatest sensitivity will normally be elongated in the direction of light transmission and cylindrical waveguides will usually be used. Moisture is supplied by means of a porous material such as a wetted sponge which is contained in a cavity adjacent the waveguides.

FIG. 1 describes a rectangular embodiment of the invention. Rectangular container 10 has holes 11 providing for the entry or exit of fluid sample to container 10. Hinges 12 and 13 together with a hinge portion (not shown in FIG. 1) on top 28 provide means for opening and closing the top on the container. Fastener 15 on top 28 cooperating with fastener 14 on container 10 provide for holding the top closed on the container. A removable frame 16 is sized to be placed in container 10 and this frame 16 has an opening 20 through a central portion and communicating with holes 11 and 27 in the container and top when the frame is in place in the container with the top closed. In the sides of frame 16 are openings 17 and 18 for receiving porous materials 22 and these openings 17 and 18 communicate with opening 20. Notches 19 are provided along opposing edges of opening 20 to receive waveguides 23. Rigid strips 24 having tips 25 which communicate with openings 21 serve to hold waveguides 23 in place in the notches on the frame. Raised portions 26 on strips 24 serve as spacers between top 28 and strips 24.

FIG. 2 shows an embodiment of the invention especially designed to attach to clothing, e.g. a coal miner's cap, by clips 33. Container 30 and top 32 form the outer case of the holder and conveniently top 32 is threaded as at 42 to mate with the threaded portion 43 of container 30 to close the holder. Top 32 has a cylindrical stem 37 depending from the top and the stem has a flange 39 at the bottom end of the stem. Spring 38 is positioned around the upper end of stem 37 and adjacent the top. Between spring 38 and flange 39 and around stem 37 is positioned hollow cylindrical frame 36. Frame 36 has flanges 41 and 44 at the top and bottom, respectively, of the frame, and the frame has notches 45 on the under sides of flange 41 and holes 46 through flange 44 to receive waveguides 40. Openings 31 in the side of container 30 serve to provide entry ports for fluid samples and screening material 35 covers the openings to exclude particulate matter such as coal dust. Screening material 35 which can be a screen or other porous material such as a membrane with openings sized to exclude at least most undesirable particulate material can also conveniently cover and hold in place porous material 34 which humidifies the container.

In order to cover the desired dynamic ranges for a pollutant of interest different concentrations of reactants incorporated into the waveguide coatings are prepared. In the case of $NH_3$ different concentrations of ninhydrin are incorporated into a waveguide coating such as polyvinylpyrollidone (PVP) which imparts the required properties.

Previous data have shown that even at high concentrations of ninhydrin the coated waveguide's response to $NH_3$ is low at low relative humidities because this is a moisture sensitive reaction. However, when the coated waveguides are placed in the described humidifier the sensitivity is improved markedly. FIGS. 3A and 3B show this at two different loading of ninhydrin in the coated waveguide. In these figures response to the coated waveguides (Absorbance) versus Exposure Time at different relative humidities and ninhydrin loading is shown with and without the use of the humidifier.

Additional beneficial effects are obtained from the use of the humidifier since it has been found that over wide ranges of relative humidities and integrated values (ammonia concentration × time) constant sensitivity is obtained which had not been possible previously. These benefits are illustrated in FIGS. 4A and 4B which shows no difference in sensitivity due to relative humidity. Curves 4A and 4B show that this condition of constant sensitivity holds for two different loadings of ninhydrin over a wide range of integrated ammonia exposure values (ammonia concentration × time). The humidifier was used for all the data points obtained in FIGS. 4A and 4B which show the response of the coated waveguides (absorbance) to $NH_3$ versus ammonia concentration × time at different relative humidities.

Many reactions are moisture sensitive and some other moisture sensitive reactions are: (1) hydrogen cyanide + sodium picrate, (2) hydrogen sulfide + lead acetate, (3) carbon dioxide + sodium carbonate/bicarbonate buffer and a methyl red indicator, (4) sulfur trioxide + barium chloride, hydrogen chloride + indicators such as phenol red or siver nitrate.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. For example, modifications can be in the design and arrangement of parts of the waveguide holder-humidifier to make the holder-humidifier an integral part of a gradient light analytical detector rather than as an accessory thereto, if desired. Accordingly, modifications are contemplated which can be made without departing from the spirit of the described invention.

What is claimed is:

1. In a method for detecting a first material wherein there are the steps of
    (a) exposing an elongated waveguide having on a longitudinal peripheral surface of said waveguide a second material providing for multiple internal reflections of light through said coating material, to an unknown material which may contain said first material, said second material upon being contacted with said first material selectively combines in in a water sensitive reaction with said first material to measurably change the light transmitting capabilities of said waveguide;
    (b) transmitting light through said waveguide after exposure in step (a); and,
    (c) detecting the light transmitted in step (b) as a measure of said first material, the improvement comprising increasing the sensitivity of detection in step (a) by maintaining said waveguide in an environment of substantially constant relative humidity at which said reaction is not appreciably affected by changes in ambient relative humidity.

2. A method according to claim 1 wherein said first material comprises gaseous ammonia.

* * * * *